(12) United States Patent
Simard et al.

(10) Patent No.: US 8,577,629 B2
(45) Date of Patent: Nov. 5, 2013

(54) METHOD AND SYSTEM FOR TRANSDUCER ELEMENT FAULT DETECTION FOR PHASED ARRAY ULTRASONIC INSTRUMENTS

(75) Inventors: Christian Simard, Quebec (CA); Michael Drummy, North Reading, MA (US)

(73) Assignee: Olympus NDT, Waltham, MA (US)

( * ) Notice: Subject to any disclaimer, the term of this patent is extended or adjusted under 35 U.S.C. 154(b) by 1229 days.

(21) Appl. No.: 12/411,303

(22) Filed: Mar. 25, 2009

(65) Prior Publication Data

US 2010/0242613 A1    Sep. 30, 2010

(51) Int. Cl.
*G01N 29/04* (2006.01)

(52) U.S. Cl.
USPC ............. 702/58; 702/104; 702/116; 73/626; 73/641; 73/614

(58) Field of Classification Search
USPC ............. 702/58, 104, 116; 73/626, 641, 614
See application file for complete search history.

(56) References Cited

U.S. PATENT DOCUMENTS

| | | | | |
|---|---|---|---|---|
| 4,176,337 A | * | 11/1979 | Aechter et al. | 367/138 |
| 4,271,707 A | * | 6/1981 | Lakin | 73/614 |
| 5,122,806 A | | 6/1992 | Julian | |
| 5,331,855 A | * | 7/1994 | Takashita et al. | 73/602 |
| 5,530,449 A | | 6/1996 | Wachs et al. | |
| 5,841,394 A | | 11/1998 | Sterns et al. | |

OTHER PUBLICATIONS

Search Report issued by European Patent Office in connection with corresponding No. EP 10 15 2012 on Jul. 15, 2010.

* cited by examiner

*Primary Examiner* — Jonathan C Teixeira Moffat
*Assistant Examiner* — Hien Vo
(74) *Attorney, Agent, or Firm* — Ostrolenk Faber LLP

(57) ABSTRACT

A method and system related to phased array ultrasonic systems identifies faults in individual element on a regular basis. The method and system are based on a simple approach of calculating energy levels in response signals from each individual element and then identifying any discontinuities or unexpected drops in energy levels sensed during a typical phased array operation, by comparing responses for individual transducer elements to the group response.

17 Claims, 11 Drawing Sheets

METHOD AND SYSTEM FOR TRANSDUCER ELEMENT FAULT DETECTION FOR PHASED ARRAY ULTRASONIC INSTRUMENTS

FIELD OF THE DISCLOSURE

The present disclosure generally relates to a method and system for monitoring the performance of phased array ultrasonic instruments, and more particularly, to fault detection on individual transducer elements of phased array ultrasonic systems.

BACKGROUND OF THE DISCLOSURE

Ultrasonic instruments that use multi-element phased array transducers provide higher inspection efficiency compared to instruments using only single element transducers. As is well known by those skilled in the art, a stationary phased array transducer can cover a larger inspection region than a stationary single element transducer because the phased array transducer emission beam axis can be electronically steered to cover a two-dimensional sector area, or three-dimension volume, by applying successive pulse-receive cycles with different focal laws—i.e. performing an S scan. Single element transducers are only capable of emission along a single beam axis.

Furthermore, when performing inspections requiring only a single beam axis (i.e. A scan), a single element transducer requires the fastening and removal of a specific angle wedge to cover more than one incident beam angle; whereas, the phased array transducer can change the incident angle electronically.

Accordingly, the single element transducer inspection method is less efficient because it requires the operator to physically move, or otherwise adjust and modify, the transducer in order to cover the same area, or range of beam angles, that a phased array transducer can in a stationary position.

There are, however, significant problems associated with conventional phased array instruments concerning inefficient detection of faulty elements and their effect on measurement data accuracy.

Ultrasonic phased array transducers are comprised of an array of small sensor elements, each of which can be pulsed individually in accordance with focal laws to steer and focus excitation signals, and focus reception signals. The response signals from multiple elements of a phased array transducer are summed together to produce an A scan for analysis and sector, or linear, scan image rendering. If one or a few elements are faulty, there will be an error in the summed response; however, the error may be difficult to discern because it is only a small part of the total sum. A faulty single element transducer does not have this problem because it is the sole signal source for the observed A-scan; therefore, unexpected signal responses can be easily discerned.

The term 'faulty' in the present disclosure is defined as an element having little or no response to an incident echo signal as compared to neighboring non-faulty elements.

The accuracy and efficiency of the phased array inspection process is of high importance because costly repair and maintenance decisions are made based on the presumed accuracy of the measurement data, and the cost associated with the inspection itself can be substantial. Accordingly, performing these inspections without being aware of the presence of a faulty element, or elements, can have a significant unfavorable effect on the validity of the inspection measurement data.

Conventional solutions for detecting faulty elements exist; however, they employ time consuming calibration processes that require the inspection process to cease when conducted, thereby reducing efficiency.

Another solution that is taught in U.S. Pat. No. 5,572,219 discloses a method and apparatus that generates calibration data for each element of a phased array transducer by comparing the reading from each transducer element when a calibration is applied with a set of predetermined data that is expected to be obtained for each element.

The problem with this and other existing calibration technologies is that complete calibrations of phased array instruments are not performed on a frequent basis; therefore, the transducer performance is not monitored between calibration sessions.

It would therefore be beneficial to provide a simple and systematic method for automatic detection of faulty phased array transducer elements on a continuous basis without unfavorable impact on the accuracy or efficiency of the inspection process.

It should be noted that the advantages of the present disclosure can also be applied to phased array measurements methods other than the S scan, such as, but not limited to, linear scans and dynamic depth focusing.

SUMMARY OF THE DISCLOSURE

The embodiments disclosed herein solve the aforementioned problems related to phased array ultrasonic systems.

The embodiments of the present disclosure relate to the measurement of energy in the echo response signal sensed by each active transducer element, and the subsequent identification of discontinuities between neighboring active elements that are indicative of a transducer element fault. This process can occur concurrently with the normal phased array system operation in order to prevent reducing the efficiency of the inspection process.

In each embodiment of the present disclosure, a calculation is performed on digitized reception signals to determine the amount of energy sensed by each active element during a predetermined period of time. The calculation is performed for a series of contiguous time periods within a pulse-receive cycle to ensure that the echo response event is not missed. It should be noted that other methods can be used to determine the amount of energy sensed by a transducer element including both analog and digital signal processing techniques that are well known to those skilled in the art. For example, an amplitude detector with, or without, a timer or counter, may be used. Alternatively, an analog integrator may be used.

The energy level calculated for each element, $E(i)$, is then compared to neighboring elements to determine the presence of the aforementioned discontinuity.

Accordingly, it is the general object of the present disclosure to provide a method and system for transducer element fault detection that can be conducted automatically and concurrently with a normal phased array inspection operation without diminishing the efficiency or accuracy of the phased array inspection process. It should be noted that the methods of the present disclosure can also be applied interactively by means of the user interface—i.e. in a non-automatic manner.

It is further an object of the present disclosure to provide a method and system for transducer element fault detection for a phased array system that can be implemented economically by adding computing programs into an existing phased array system without the need for making substantial changes to hardware.

The foregoing and other objects, advantages and features of the present disclosure will become more apparent upon reading of the following non restrictive description of illustrative embodiments, given for the purpose of illustration only with reference to the enclosed drawings.

DETAILED DESCRIPTION OF EMBODIMENTS OF THE PRESENT DISCLOSURE

General Information

The present disclosure pertains to the automatic detection of faulty phased array transducer elements by analyzing the echo energy level received by each element and detecting substantial energy level discontinuities between neighboring elements.

The present disclosure also pertains to phased array transducers with two or more elements that may be arranged in a linear or two-dimensional configuration.

Although the embodiments of the present disclosure are described in the context of a conventional pulse-receive phased array system wherein the pulse event and reception event occur at different times, they apply also to a continuous wave phased array system wherein emission and reception occur simultaneously. The energy received by the elements in a continuous wave system contains both emission and reception signals that are separated during the reception process by means of demodulation.

It should be noted that the following lexicon applies to the present disclosure:

The term 'energy' as used in the present disclosure applies to the transducer element voltage response used for energy level calculation; however, those who are skilled in the art will appreciate that units other than voltage may be used such as, but not limited to, current, coulombs, or watts, for the purpose of energy level calculation.

The term 'active element' or 'active transducer element' shall mean an element within a phased array transducer array that is used for signal reception. It should be noted that it is not uncommon for only a subset of the total number of transducer elements to be active in a phased array system.

The term 'neighboring' shall mean a grouping of two or more contiguous active elements.

The term 'discontinuity', or 'discontinuities', shall mean a substantial difference, or differences, in energy level between neighboring transducer elements.

The term 'pulse-receive cycle' shall mean an event that starts coincident with the emission of a set of focalized pulsers and ends prior to the next emission.

The term 'acquisition period' shall mean an event that begins at the start of the pulse-receive cycle using the first focal law, and stops at the end of the pulse-receive cycle using the last focal law. The number and range of focal laws is typically determined by the number of beam angles included in an S scan, or the number of beam positions for a linear scan.

The term 'faulty' shall mean an active element having little or no response to an incident echo signal as compared to neighboring non-faulty elements.

Unless otherwise stated, the present disclosure pertains to the preferred embodiment.

Use Scenario for Invention

The following explanation of the acoustic and electronic activity associated with conventional phased array system operation is intended to help the reader understand the context in which the present disclosure applies.

Figure 1:
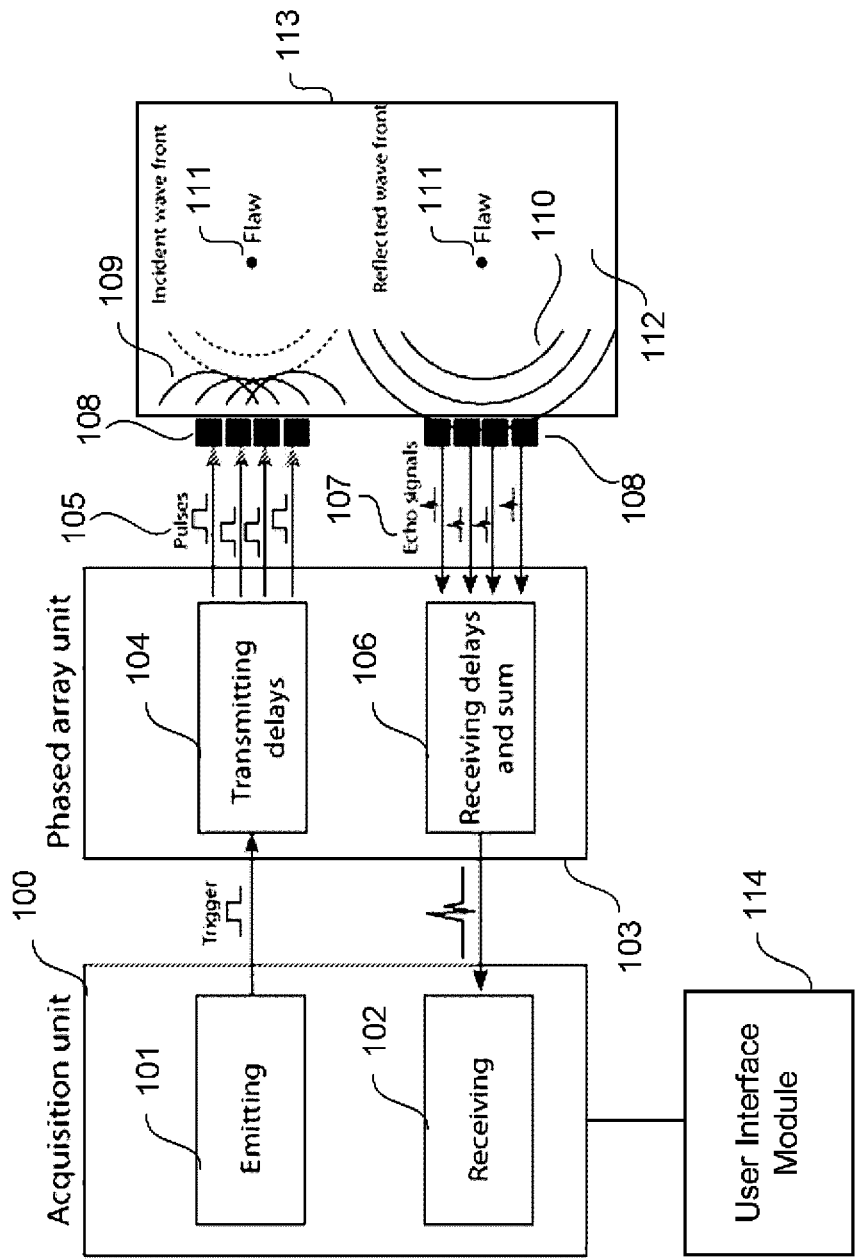
FIG. 1 is a diagram showing an exemplary phased array inspection system of the present disclosure.

Referring to the exemplary phased array inspection system of FIG. 1, it should be noted that although only four elements are shown for transducer 108, conventional phased array transducers typically may have many more elements. It is not uncommon for a phased array transducer to have one hundred and twenty-eight, or more, elements. The methods and systems of the present disclosure are not limited with respect to a maximum quantity of elements.

Continuing with FIG. 1, the pulse-receive cycle starts when transducer elements 108 are energized by pulses 105 in accordance with the focal law provided by transmitting delays 104. This results in the emission of incident wave front 109 in test object 112. When incident wave front 109 encounters flaw 111, or perimeter 113 of test object 112, an echo is reflected back toward elements 108.

To simplify description of the echo reception event, flaw 111 and elements 108 are depicted again in a separate view accompanied by reflected wave front 110 and echo signals 107. Reflected wave front 110 is sensed by elements 108 resulting in echo signals 107 that are provided to module 106 for focal law delay application and subsequent summing to produce an A scan.

It should be noted that emission of focal law pulses 105 is triggered by emitting module 1301, and that the A scan is processed by receiving module 102, both of which are contained in acquisition unit 100.

Detailed Description of the Preferred Embodiment of the Present Disclosure

The embodiments of the present disclosure all require that a sufficient transducer element energy level be received before reliable faulty element detection can be achieved. The following considerations need to be made to ensure optimal conditions for sensing the energy level of phased array transducer elements.

An element blind spot occurs when a substantial energy level is sensed by only a portion of the elements within a phased array transducer because the energy is emitted in a direction that does not result in sufficient reflected energy in the direction of the element blind spot.

An example of an element blind spot is now described with reference to FIGS. 2 and 3. It can be seen that when focal law delay magnitudes 201 are applied to their corresponding elements of phased array transducer 202, incident wave front 204 propagates in a direction normal to the top surface of test object 203—i.e. at 0 degree beam angle 205. When flaw 207, or back wall 206 of test object 203, is encountered, an echo (not shown) travels back to phased array transducer 202, the elements of which sense an incident energy distribution similar to the magnitude distribution contour of focal law delays 201. The resulting received energy level profile has a bell shaped curve similar to the contour of 201, with most of the energy received by the center elements (e.g. elements 6 through 11). Accordingly, a bell shape curve energy level profile is conducive for the detection of faulty elements located in the center region of the transducer array because there is more energy present to discriminate energy level discontinuities as compared to the blind elements located at the sides of the bell curve (e.g. elements 1 through 5, and 12 through 16).

Figure 3:
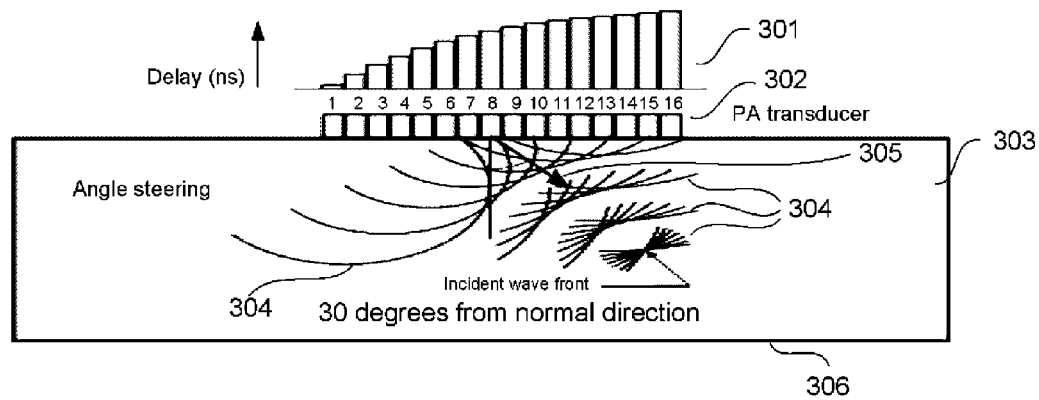
FIG. 3 is a diagram showing an example of applied focal laws for a typical phased array operation that steers the acoustic beam at a 30 degree angle.

The problem of reliable fault detection for elements located near the sides of the transducer array is overcome by the method described now for FIG. 3. An explanation is provided only for the elements located on the right side of the transducer array because the explanation is also valid for the left side due to symmetry.

Figure 2:
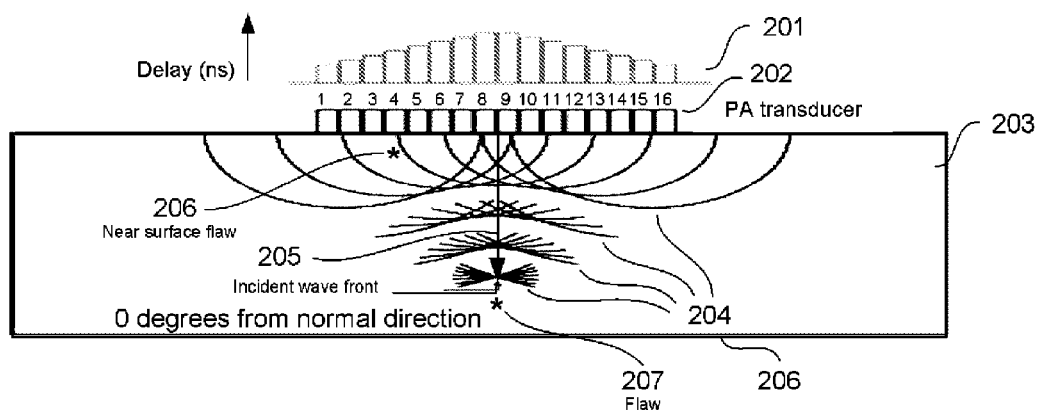
FIG. 2 is a diagram showing an example of applied focal laws for a typical phased array operation that steers the acoustic beam at a 0 degree angle.

It can be seen that when focal law delay magnitudes 301 are applied to their corresponding elements of phased array transducer 302, beam steering occurs resulting in incident wave front 304 propagating at an angle of 30 degrees to the right of normal beam 205 of FIG. 2. When a flaw (not shown), or back wall 306 of test object 303, is encountered, the reflected echo (not shown) travels back to phased array transducer 302 which senses an incident energy level distribution similar to the magnitude distribution contour of focal law delays 301. The resulting echo energy level profile has a rising left to right shaped curve similar to the contour of 301, with most of the energy received by the right most elements (e.g. elements 12 through 16).

A rising left to right shape curve energy level profile is conducive for the detection of faulty elements located on the right side region of the transducer array because there is more energy present to discriminate discontinuities as compared to the blind elements located at the opposite side (e.g. elements 1 through 5).

Accordingly, the embodiments of the present disclosure can employ beams at different angles to ensure that all transducer elements can emit and receive the most energy possible for the purpose of determining energy level discontinuities across all of the elements of a given transducer.

Element Energy Level Measurement

The next important aspect of the present disclosure for the reader to understand is how the energy level of each element is measured by means of a calculation that is applied to signals sampled during a pulse-receive cycle.

It is worth noting that the energy level calculation method provides significant noise immunity advantages over simple signal voltage sampling because it is calculated using a plurality of samples, thereby minimizing the impact from occasional spurious noise signals.

The method for processing the energy level calculations to determine the presence of discontinuities indicative of a faulty transducer element is described later in the present disclosure.

Figure 4:
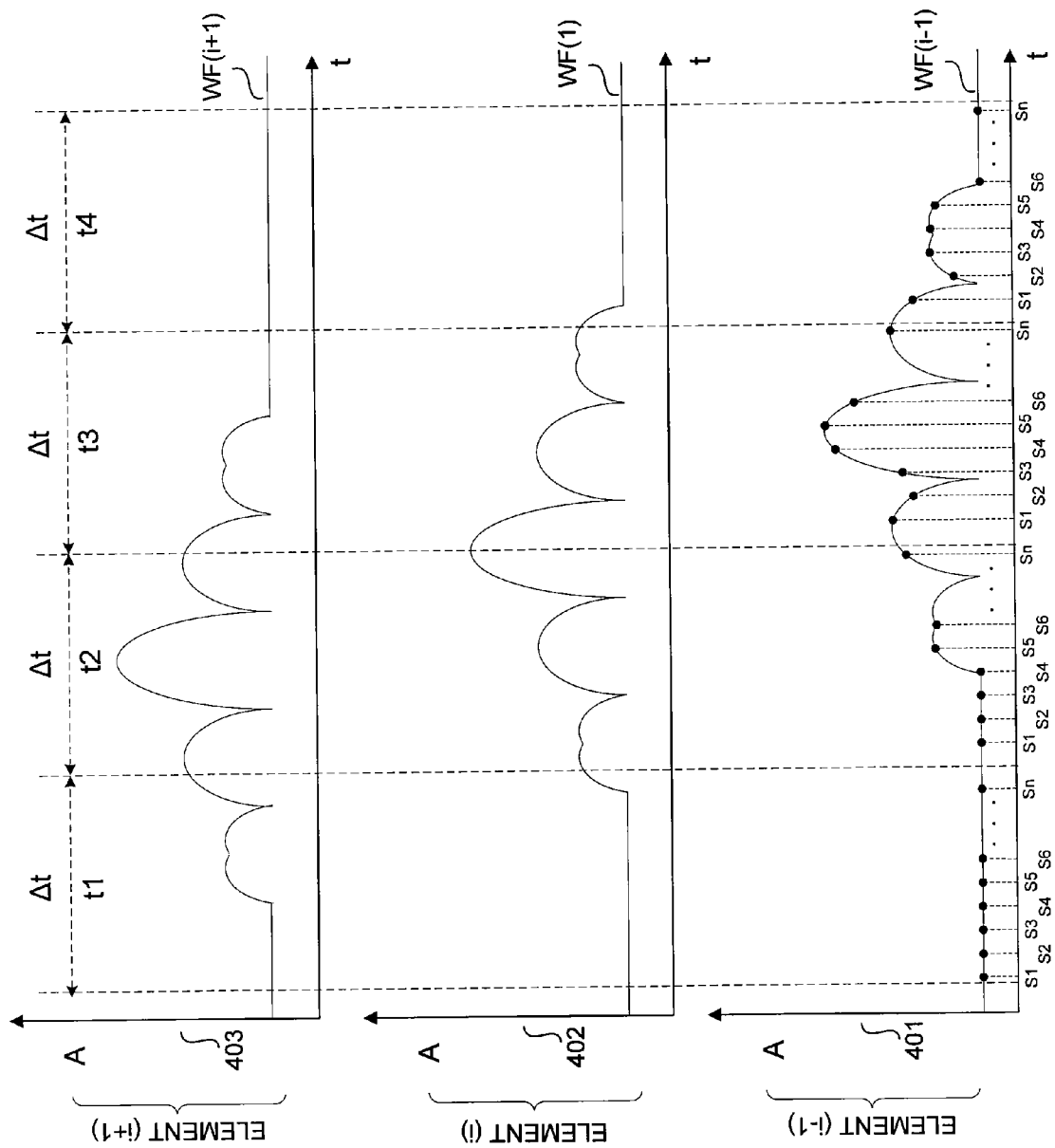
FIG. 4 is a diagram showing three out of phase received waveforms.

Graphs 401, 402, and 403 of FIG. 4 depict three concurrent reception events within a pulse-receive cycle. Waveforms WF(i−1), WF(i), and WF(i+1) are provided by neighboring elements within a phased array transducer.

Time period t1 starts just after the pulser emission event because it is possible that the pulser energy level sensed by each element will exceed the full scale limit of analog to digital conversion system 703 (FIG. 7), or the pre-amplifiers at its input (not shown), thereby causing saturation. Once saturation occurs, the relationship of the amplitude data provided by ADC's 703 with respect to the signals sensed by elements 702 becomes non-linear; consequently, the accurate amplitude measurements required to determine element energy level, E(i), cannot be made.

In the event the pulser energy sensed by each element produces amplitudes that are within the linear region of operation (i.e. not saturated), the amplitudes can be much greater than that of the echoes received from the test object. Consequently, the pulse-receive system of the present disclosure will be desensitized to these echoes because E(i) will be disproportionately weighted by the pulser energy.

It should be noted that for a continuous wave phased array system, the time period shown for the waveforms of FIG. 4 need not exclude emission event.

Continuing with FIG. 4, all Δt time periods and the sampling process within them are equivalent. The following explanation of the sampling process provided for graph 401 applies to all waveform (WF) graphs appearing on FIGS. 4, 7 and 9.

Each Δt time period has n samples (S1 through Sn) and is calculated using Eq. 1 below.

$$\Delta t = \frac{n}{F_s} \qquad \text{Eq. 1}$$

where:
'Δt' is the time period during which receive signal data is sampled and energy level, E(i), is calculated;
'n' is total number of samples during time interval Δt;
'Fs' is the sampling frequency of normal phased array operation.

For the calculation of E(i) for each element, it is further defined that,
'N' is the total number of active transducer elements;
'i' is the active transducer element identifier from N elements;
'$A_{ij}$' is the receive signal sample amplitude value of active element number i at the $j^{th}$ sample from the start of Δt;
E(i): calculation of the energy level provided by active element i.
Therefore, E(i), for the number i element during time interval Δt defined by the following equation:

$$E(i) = \frac{1}{n}\sum_{j=1}^{n} A_{i,j}^2, \text{ over } \Delta t \qquad \text{Eq. 2}$$

Although the various WF waveforms depicted in the figures of the present disclosure are all shown with positive amplitude values, it should be noted that bipolar signals may also be sampled, in which case the squaring of variable $A_{ij}$ will allow both positive and negative signal samples to increase the summed value of E(i).

Figure 5:
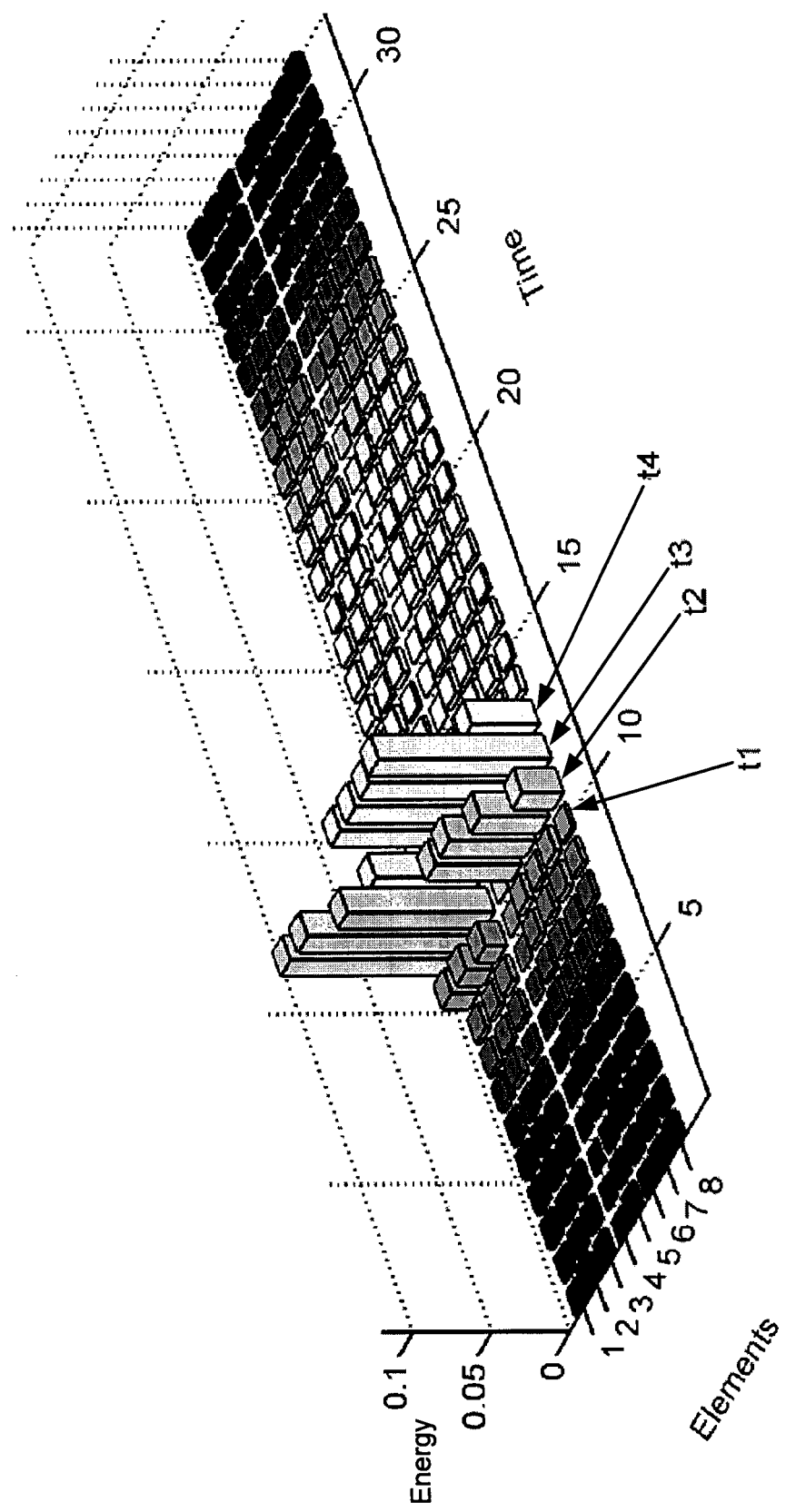
FIG. 5 is a three dimensional diagram showing the energy level bars of eight elements during a period after the elements are pulsed.
Figure 6:
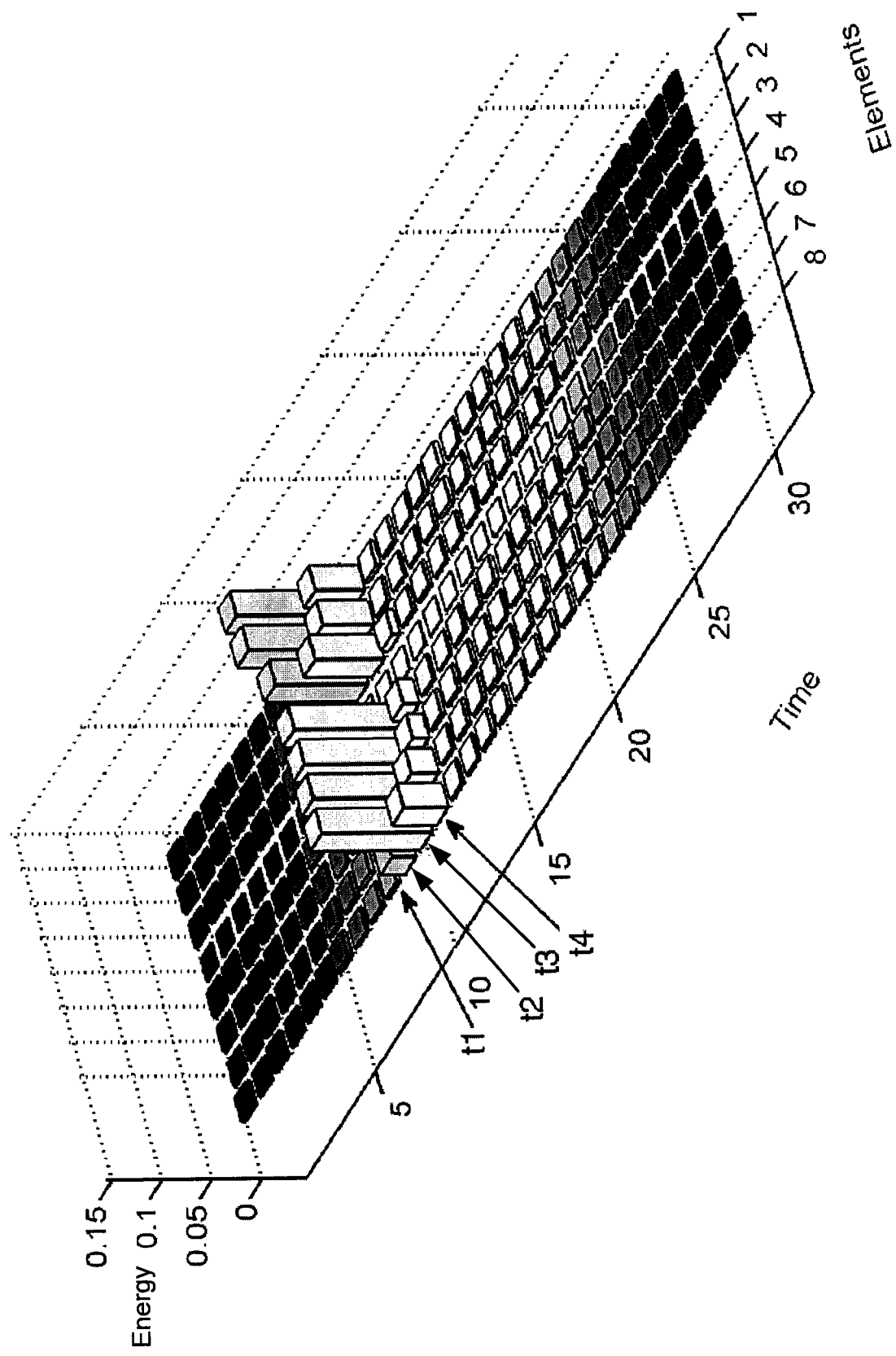
FIG. 6 is a three dimensional diagram showing the rearview of the energy level bars of FIG. 5.

FIGS. 5 and 6 provide an exemplary three dimensional front view and rear view, respectively, of the E(i)'s resulting from applying the methods of the present disclosure. The three dimensions are element #, time, and energy level. A substantial energy level discontinuity can be seen for element 4 for time periods t2 and t3, whereas, it cannot be easily discerned for time periods t1 and t4. The method of discernment is described in detail below.

Energy Level Profiling Method

Figure 7:
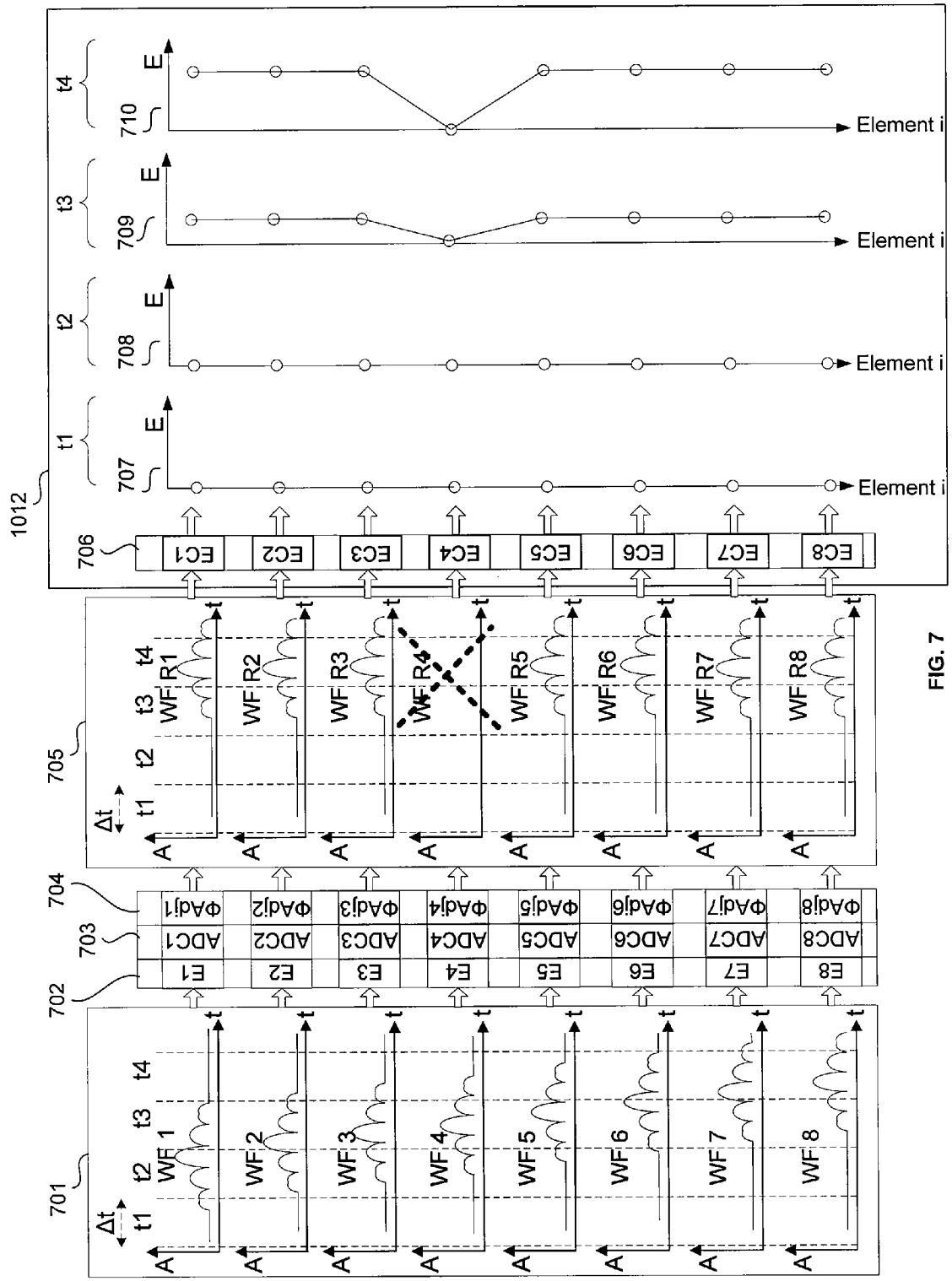
FIG. 7 is a diagram showing eight elements and signal processing modules, along with the resulting graphs of the energy level during four Δt time periods.

Referring to the exemplary phased array system of FIG. 7, N of Eq. 2 equals eight active elements, input waveforms WF1 through WF8 701 are received by elements E1 through E8 702, the signals from which are provided to analog to digital converters ADC1 through ADC5 703 for sampling. The phase of the digitized outputs of 703 are subsequently aligned by focal law phase adjust 704 to produce digitized waveforms 705 for E(i) calculator 706. In the preferred embodiment, this process is applied to each element, i, of the N active elements independently and concurrently. It should be noted that the methods disclosed for the preferred embodiment may be applied without the use of focal law phase adjust 704 by providing the digitized outputs of 703 directly to E(i) calculator 706.

As can be seen by graphs 707, 708, 709 and 710 associated with Δt's t1, t2, t3 and t4, respectively, the magnitude of E(i)'s change from one Δt period to another. E(i)'s of substantial magnitude do not appear prominent until t4 is reached in graph 710; therefore, all E(i) values for each Δt period must be processed and analyzed together to ensure that the E(i)'s of sufficient magnitude are captured to detect faulty element E4.

Figure 10:
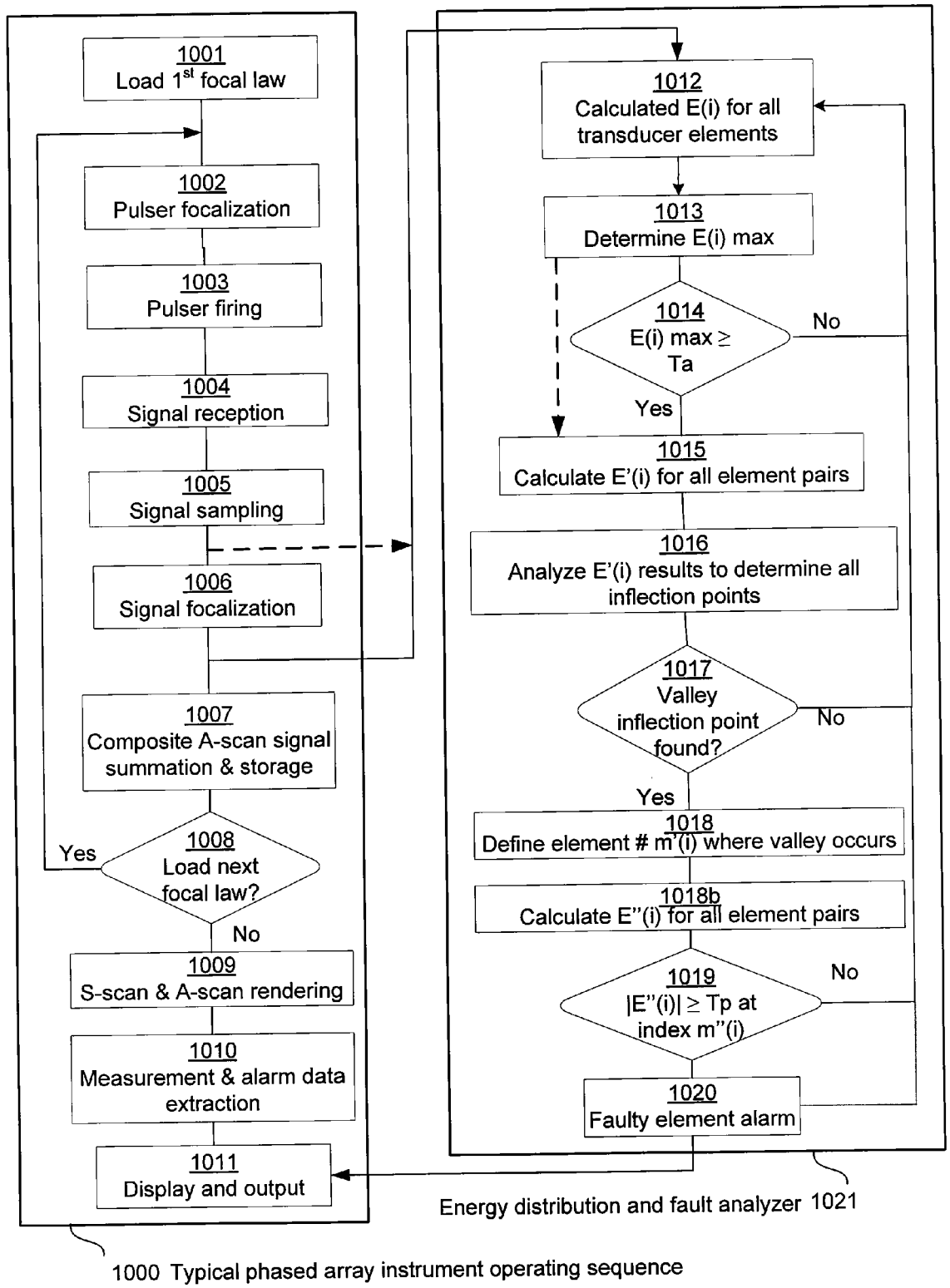
FIG. 10 is a diagram showing the sequence of operations associated with a conventional phased array instrument and the operations associated with embodiments of the present disclosure.

The processes associated with E(i) calculator 706 and the producing of graphs 707, 708, 709 and 710 take place within functional block 1012 of FIG. 10.

'Energy Envelope' Alternate Embodiment

The 'Energy Envelope embodiment' is now introduced and the problems it is intended to overcome are described in order to provide background for the description of the preferred embodiment continued afterwards. A detailed description of the 'Energy Envelope embodiment' is provided later in the present disclosure as well.

As compared to the preferred embodiment, the energy envelope embodiment provides the advantage of reducing system real-time processing activity to conserve power and simplify design. This alternate embodiment also allows for faulty element detection when E(i) is calculated using the sample data of non-phase compensated reception signals. More specifically, as shown FIG. 7, the digitized outputs of analog to digital converters 703 are provided directly to energy level calculator 706, instead of through phase adjusters 704 as is done in the preferred embodiment. Consequently, the problem associated with 'out of phase echoes' may arise.

To illustrate this problem in FIG. 4, exemplary element reception waveforms WF(i−1), WF(i) and WF(i+1) are identical except for the phase relationship between them. It can be seen that during time period t2 that WF(i+1) will have the maximum E(i), WF(i−1) will have the minimum, and WF(i) will be somewhere in between; however, they are known to be identical except for phase. The most extreme example in FIG. 4 of the adverse effect of differing phase relationships can be seen in Δt periods t1 and t4, where there is no echo waveform for WF(i+1) in t4 and none for WF(i−1) in t1. Accordingly, even if the waveforms differ in amplitude, substantial errors can still occur.

For these reasons the comparison of E(i) values during a specific Δt (i.e. t1, t2, t3 or t4) can provide skewed results for out of phase waveforms regardless of their respective magnitudes, and thereby adversely affect the reliability of element fault detection if not overcome by other methods.

In the energy envelope embodiment, the maximum E(i) for each element during a complete pulse-receive, or acquisition, cycle is used for the identification of discontinuities between neighboring elements. This method will ameliorate the aforementioned phase problem because the phase relationship between Δt time periods and echo response signals will not be constant from one pulse-receive cycle to another when the focalized beam angle is changed, or the transducer is moved over the test object. Accordingly, many different phase relationships between neighboring elements will be measured over the longer observation period; therefore, the probability of obtaining valid E(i) measurements for waveforms WF(i−1), WF(i) and WF(i+1) will be much higher.

Problem of Multiple Echoes for 'Energy Envelope' Alternate Embodiment

A drawback of the energy envelope embodiment can appear when there is more than one echo event within a given pulse-receive cycle and there is no means to detect this. Specifically, the maximum E(i) for a faulty element may result from a second flaw echo that has much higher amplitude than the echo that produces the maximum E(i) for the neighboring non-faulty elements. Even if the element is faulty, the higher echo amplitude may be sufficient to compensate for its insensitivity and produce a E(i) that gives the appearance of a continuous magnitude contour along neighboring elements.

Referring to FIG. 2, near surface flaw 206 is located in close proximity to element 4 of transducer 202 as compared to flaw 207. Near surface flaw 206 is very small in size in comparison to the surface of element 4 and is located before the focal point of incident waveform 205; therefore, its echo energy level will be significantly attenuated before being sensed by neighboring, or any other, elements. Consequently, if element 4 is faulty to the degree it has a substantially attenuated response compared a 'good' element, the echo energy level sensed by element 4 for near surface flaw 206 can be comparable in magnitude to its neighboring elements that sense the echo from flaw 207. Accordingly, the faulty element would not be detected because the system would respond as if the response of element 4 was satisfactory.

The problem of receiving more than one echo per pulse-receive, or acquisition, cycle can also make a non-faulty element appear faulty if a discontinuity is produced between neighboring elements by the varying echo amplitude behavior described above. This could be caused by a series of near surface flaws (not shown) located under a number of the elements in transducer 202.

'Energy Envelope with Echo Location' Alternate Embodiment

Methods may be employed to detect this behavior that will prevent both false, and missed, detection of a faulty element. Specifically, the approximate location in time of each echo can be measured and used as a criterion along with E(i) to ensure that the faulty element detection method is applied to the same echo for all elements. Accordingly, this would eliminate the aforementioned risk due to comparing E(i) values across elements from different echoes. This augmentation of the energy envelope embodiment is referred to the 'energy envelope with echo location' embodiment.

As is well known by those skilled in the art, there are many ways to determine the location in time of received echoes. The method used in the energy envelope embodiment (not shown) of the present disclosure uses a counter that starts at the beginning of the pulse-receive cycle and stores its value each time the element signal meets a predetermined E(i) value. This value is then stored until the end of the pulse-receive cycle for comparison to the values stored for other elements during the same pulse-receive cycle.

If the counter values are outside of a predetermined range, indicating that different echoes produced the maximum E(i), a faulty element alarm will not occur and a message can be sent to the user interface module 114 (FIG. 1) to indicate that that the fault detection system is inoperable.

If the counter values are inside of a predetermined range, indicating that the same echo produced the maximum E(i), a faulty element alarm will occur if certain criteria are met (described later), and a message will be sent to the user interface module 114 to indicate that a fault has been detected.

Return to Preferred Embodiment of Present Disclosure

Figure 9:
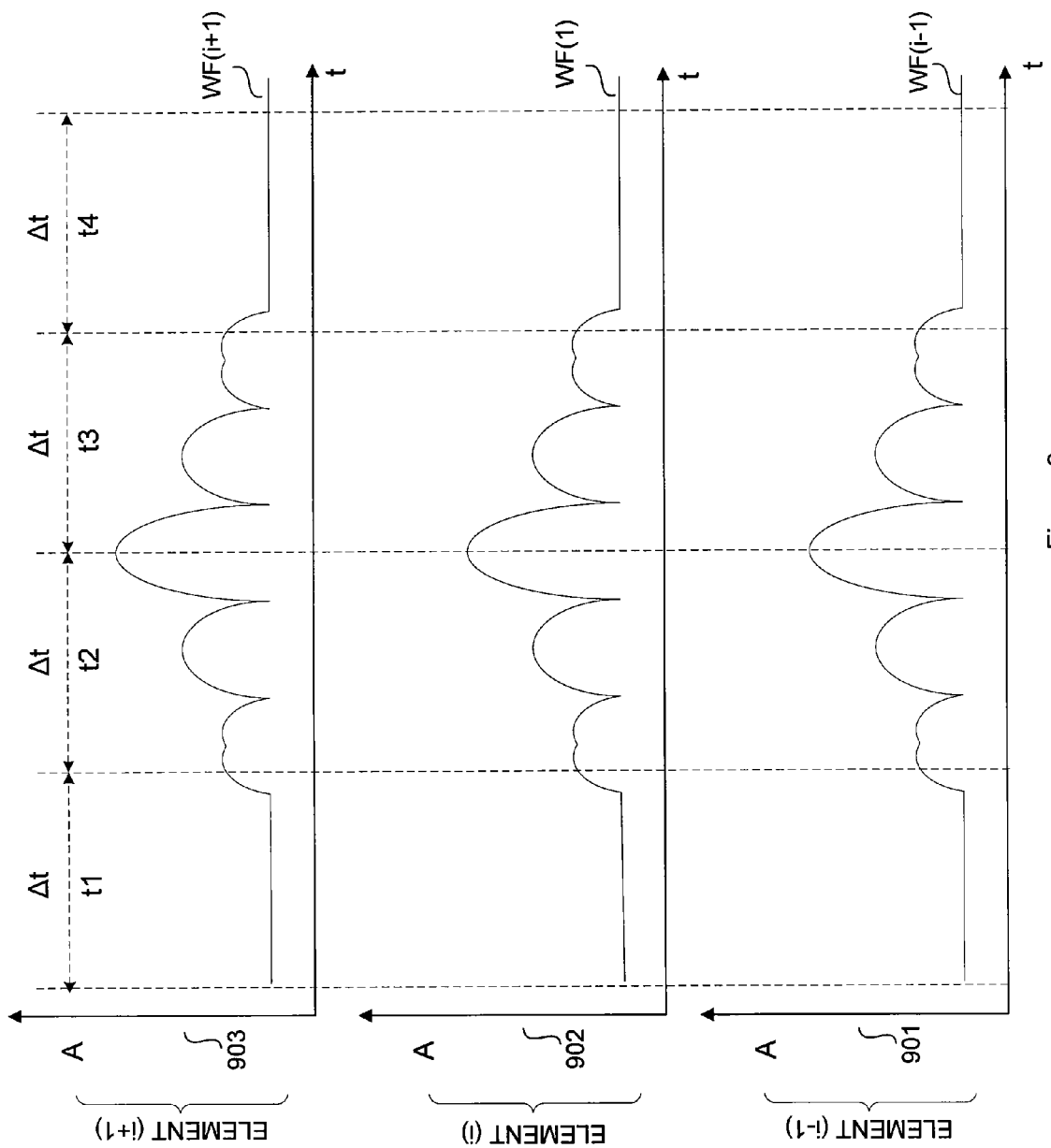
FIG. 9 is a diagram showing three phase adjusted received waveforms.

To elaborate on the earlier description of the exemplary phased array system of FIG. 7, exemplary element reception waveforms WF(i−1), WF(i) and WF(i+1) of FIG. 4 are depicted again in FIG. 9; however, this time the reception focal law delays are applied by phase adjusters 704 to phase align them.

The phase alignment of the echo response from each element eliminates the previously described problem caused by 'out of phase echoes' because it ensures that no substantial E(i) errors due to phase are present during each Δt, thereby providing the means for reliable comparison of the energy level across all elements for each Δt.

The problem described previously for the 'Energy Envelope' alternate embodiment caused by 'Multiple Echoes' is also solved because the E(i) comparisons are performed for all elements for each Δt, not over different Δt's when other echoes may be present.

It should also be noted that the time period Δt is typically sized to be less than or equal to one echo event; however, there may be cases when the opposite is required. The setting of time period Δt is primarily dependent on the following factors:
 a) Center frequency and bandwidth of focalized pulsers
 b) Center frequency and bandwidth of the transducer
 c) Bandwidth of signal reception system
 d) Amount of power, processing time, and hardware resources available to implement the present disclosure

Sequence of Operations for a Typical Phased Array System

Referring now to FIG. 10, function block 1000 depicts the sequence of operation steps associated with a typical phased array instrument shown in FIG. 1.

The process begins with step 1001 when the focal law for the first sector angle is loaded. The focal law is then applied to the transmitter time delay circuit 104 in step 1002, after which the pulses 105 are fired at step 1003 for ultrasonic emission into the test object 112. Signal reception from the transducer elements 108 then occurs during step 1004 which is in turn sampled by phased array unit 103 at step 1005, and focal law adjusted in block 106 at step 1006 before being summed and stored as a composite A-scan at step 1007 in block 106. The next focal law will be provided to phased array unit 103 at step 1002 if it is determined at step 1008 that there are any remaining angles required for rendering the sector image, or beam positions for a linear scan image.

It should be noted that steps 1002 to 1008 constitute one pulse-receive cycle, and are repeated for each S-scan beam angle, or beam position of a linear scan, to constitute an acquisition cycle.

The last steps of a typical phased array instrument operation pertain to A-scan, S-scan or linear scan rendering at step 1009, the extraction of measurement and alarm information at step 1010, ending with the update of the display and/or output with this information at step 1011. Steps 1009 and 1010 occur within acquisition unit 100, and step 1011 occurs within user interface module 114.

Sequence of Operations for the Preferred Embodiment Including

Method for Processing E(i)'s to Determine the Presence of Discontinuities Indicative of a Faulty Transducer Element Continuing with FIG. 10, energy distribution and fault analyzer 1021 is shown in concert with typical phased array instrument operating sequence 1000 in order to illustrate the operations of the element fault detection system of the present disclosure. It should be noted that graphs 801, 802 and 803 of FIG. 8 apply to sixteen elements of an exemplary phased array transducer, and that energy distribution and fault analyzer 1021 may reside within Acquisition unit 100 or Phased array unit 103 shown in the exemplary phased array inspection system of FIG. 1.

Figure 8:
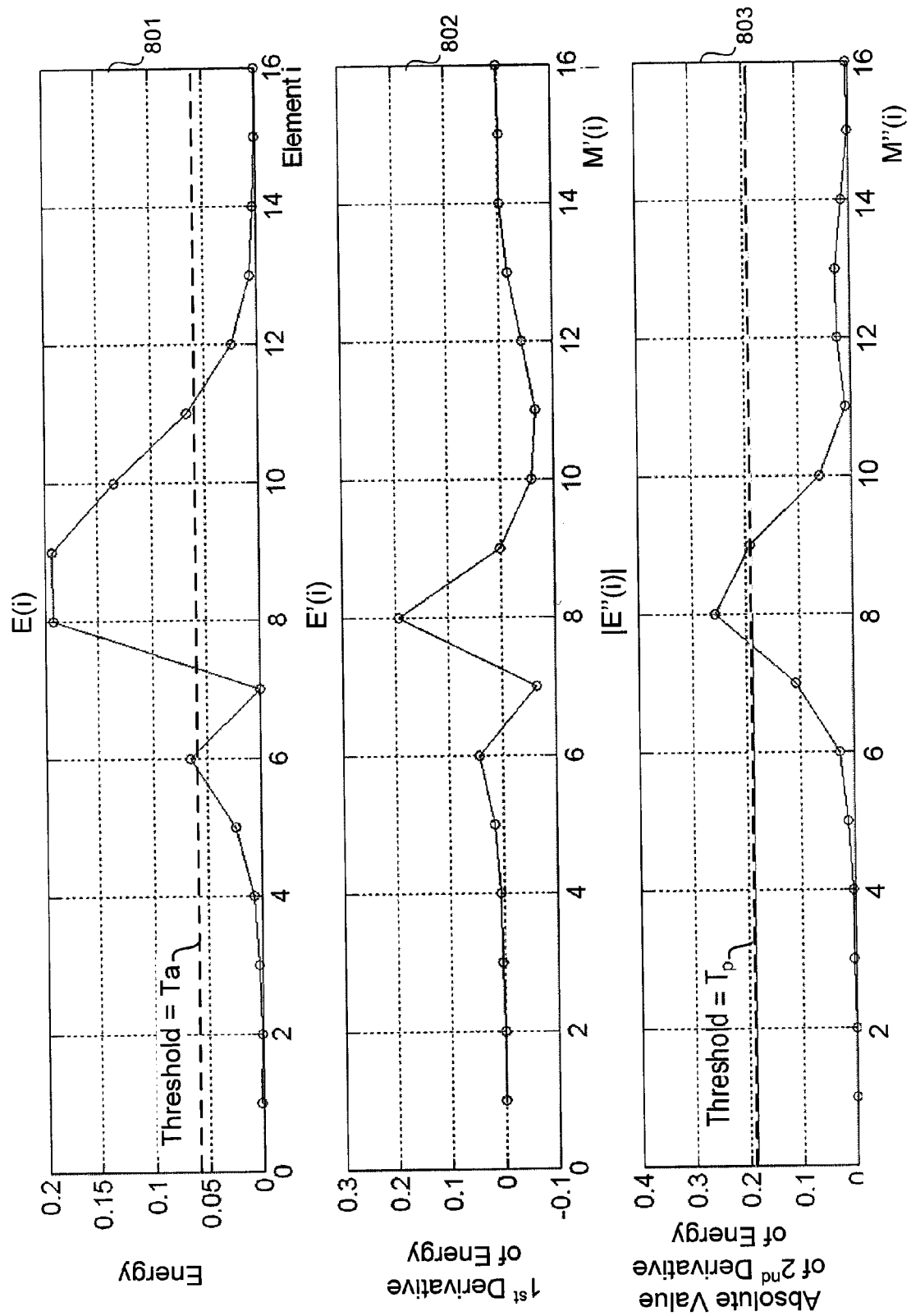
FIG. 8 shows the graph of the energy levels, across all active elements with corresponding first derivatives and second derivative absolute value.

The output of receive signal focalization step 1006 is provided for step 1012 to calculate E(i), for all transducer elements, which are then plotted on graph 801 of FIG. 8. The maximum value of E(i) is 0.2 for the exemplary embodiment.

It should be noted that for the 'energy envelope with echo location' alternate embodiment, the output of receive signal sampling step 1005 is provided instead of step 1006 to step 1012 (depicted with a dashed line) to calculate E(i) for all transducer elements which are then plotted on graph 801 of FIG. 8.

Continuing with the preferred embodiment, the maximum value of E(i) calculated during step 1012 is determined at step 1013 for subsequent comparison to the minimum acceptable threshold value, Ta, at decision step 1014. Graph 801 shows threshold Ta which sets the minimum signal to noise ratio E(i) must reach before proceeding to step 1015.

It is possible for the method described for energy distribution and fault analyzer 1021 to be realized without decision step 1014; however, its inclusion is preferred because it improves the reliability of the fault detection method. The dashed line connecting step 1013 to step 1015 is intended to show this alternate operation sequence.

Continuing with step 1014, if the minimum acceptable value for Ta is not met, step 1012 is returned to for calculation of the next set of E(i)'s. However, if the minimum acceptable value for Ta is met, the first derivative, E'(i), is calculated for each pair of adjacent active elements contained in the phased array transducer at step 1015.

E'(i) is calculated to determine the change in energy level between adjacent active elements as part of the process for identifying a discontinuity between neighboring elements. E'(i) is calculated as follows:

$$E'(i)=E(i)-E(i-1) \qquad \text{Eq. 3}$$

The result of Eq. 3 is plotted on graph 802. The maximum magnitude values of E'(i) for the exemplary embodiment are +0.2 or −0.2 because the minimum value E(i) can be is 0 and its maximum value cannot exceed 0.2.

After E'(i) is calculated for all adjacent active elements at step 1015, each set of three adjacent E'(i)'s across all active elements are compared at step 1016 to determine the presence of a negative to positive slope inflection—i.e. a 'valley'. Specifically, the slope of the line connecting E'(i−1) to E'(i) is compared to the slope of the line connecting E'(i) to E'(i+1) to determine the presence of a valley. If the slope value of the former is negative and the latter is positive, the valley is located at element i and is designated as index number m'(i). The detection of a valley is one of the two criteria used in the preferred embodiment to determine the presence of a faulty element because it is indicative of an energy level discontinuity between neighboring transducer elements.

If no valleys are detected, a decision is made at step 1017 to return to step 1012 for calculation of the next set of E(i)'s. If one or more valleys are detected, the operation moves to step 1018 to store the element index number, m'(i), where the low point of each valley occurs—e.g. element 7 shown on graph 802 in FIG. 8.

Although a valley is indicative of an energy level discontinuity between neighboring elements, it does not necessarily indicate the presence of a faulty element because the magnitude of the energy level discontinuity may not be substantial. Accordingly, the magnitude of the energy level discontinuity must be determined and subsequently compared to a minimum threshold $T_p$ to reliably detect faulty transducer elements. The meeting of this threshold is the second, and last, criteria to be met in order to indicate the presence of a faulty element.

To determine the magnitude of an energy level discontinuity, second derivative, E"(i), is calculated for adjacent E(i)'s in step 1018b as shown below in Eq. 4.

$$E''(i)=[E'(i)-E'(i-1)] \qquad \text{Eq. 4}$$

The absolute value of the result of Eq. 4, |E"(i)|, is stored and then plotted on graph 803 during step 1018b. The maximum possible value of |E"(i)| for the exemplary embodiment is 0.4 because the minimum possible value of E'(i) is −0.2 and the maximum is not greater than 0.2.

At step 1019, |E"(i)| is compared to threshold $T_p$ of graph 803 of FIG. 8 to determine whether it is of sufficient magnitude to be considered a valid indication of a faulty transducer element. The exemplary value of $T_p$=0.2.

The value of $T_p$ may be set between the maximum measured value of E(i) found among all the elements at step 1013 and two times that value, 'E(i)×2'. Increasing the value of threshold Tp closer to 'E(i)×2' decreases the probability of false faulty element detection; however, it can also decrease probability of faulty element detection. The values of Tp and Ta may be set by the instrument owner, operator, or manufacturer to optimize the values best suited for the intended applications.

If all |E"(i)| are less than Tp, a decision is made at step 1019 to return to step 1012 for calculation of the next set of E(i)'s.

If any |E"(i)| is greater than or equal to Tp, at least one of the elements associated with index numbers m'(i)'s stored during step 1018 is considered to be a faulty element, and the operation moves to step 1020 to send a faulty element alarm to user interface module 114 (FIG. 1) at display and output step 1011.

If the specific transducer element detected as faulty must be known, each index number m"(i) on graph 803 associated with an |E"(i)| that is greater than or equal to Tp can be stored during step 1019 and retrieved for analysis in alarm step 1020. If a stored index number, m"(i), minus one is equal to an element index number m'(i) associated with a detected valley in step 1017, index number m'(i) is identified as the faulty element number during alarm step 1020. This process may be applied to all m"(i)'s stored during step 1019 in order to identify all faulty elements.

In the exemplary graph 803 the value at index number 8 is the only one to exceed Tp; therefore, element 7 will be indicated as the faulty element.

The operational sequence described above for functional block energy distribution and fault analyzer 1021 occurs without interruption to the operation of typical phased array instrument block 1000. Accordingly, there is no loss of efficiency or accuracy of the system when the faulty element detection function is enabled.

Detailed Description of Alternative Embodiments of the Present Disclosure

'Energy Envelope' Alternate Embodiment

The 'energy envelope' embodiment discussed earlier, and described in more detail now, provides yet another approach to identify the sudden drop in energy level, by comparing the maximum calculated E(i) of each element over a longer period of time. Preferably, in this alternative embodiment, E(i) is computed the same way as disclosed in the preferred embodiment; however, it can be calculated much less often—i.e. only the maximum E(i) for each element is analyzed and compared to all elements.

It should be noted that the 'acquisition period' of each normal phased array operation begins at the start of the pulse-receive cycle using the first focal law, and stops at the end of the pulse-receive cycle using the last focal law. The number and range of focal laws is typically determined by the number of beam angles included in an S scan, or the number of beam positions for a linear scan.

Referring back to Eq. 2, assuming the total number of Δt during a complete typical phased array operation is m. Then the maximum value of E(i) (i.e. 'Envelope Value', EEnv(i)) for a specific element i is determined as follows.

Let κ to be the index number of Δt, where κ=1, 2, . . . , m, then, for element i, $$E_{i,k}=(E_{i,1},E_{i,2},\ldots,E_{i,k}\ldots,E_{i,m-1},E_{i,m}), \qquad \text{Eq. 7}$$

$$EEnv(i)=\max(E_{i,k}) \qquad \text{Eq. 8}$$

At the end of the pulse-receive, or acquisition, period of a normal phased array operation, the resulting envelope value for each element EEnv(i) is analyzed in the same manner as described earlier for energy distribution and fault analyzer 1020, except for the calculation performed in step 1013 which would be replaced by equations 7 and 8 performed successively. The value of EEnv(i) would then be provided to step 1014 for evaluation with respect to threshold Ta, as described above.

Figure 12:
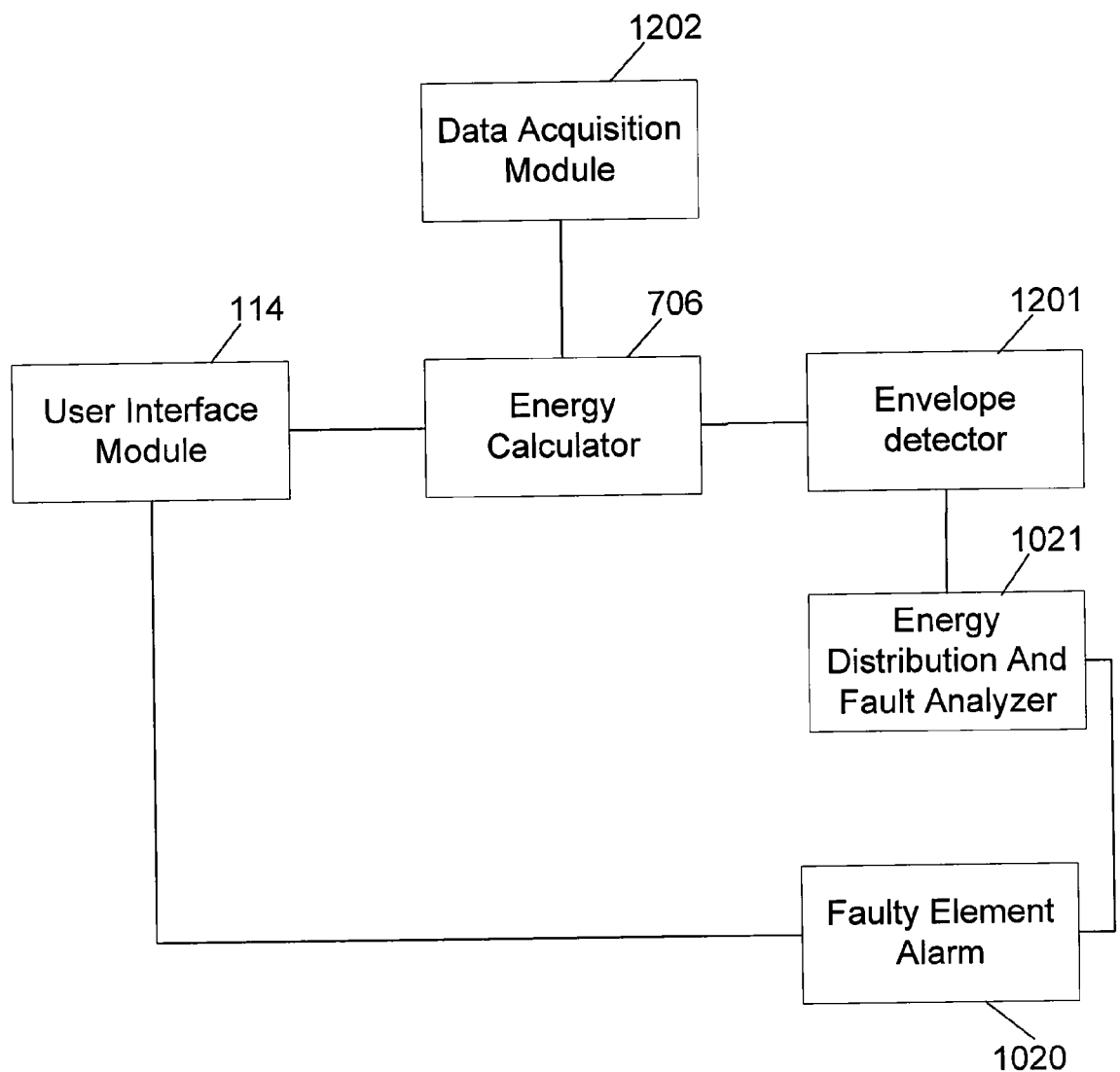
FIG. 12 is a diagram showing another alternate embodiment of the present disclosure comprising the functional modules with which the disclosed transducer element fault detection method is implemented according to energy level envelope values.

FIG. 12 shows the above alternative embodiment of the presently disclosed transducer fault instrument comprising functional modules implementing the element fault detection method described above. Echo signal data from each element sampled by analog-to-digital converters 703 (FIG. 7) is provided to data acquisition module 1202. The received signal data provided here is the same as that provided during a typical phased array testing operation. User defined parameters and threshold criterion as described above can be entered through a user interface module 114. Then the E(i) values for each element are calculated by the energy level calculator 706 according to the signal data from each element and the Eq. 2 as described above. Subsequently at envelope detector 1201, the envelope value, EEnvi, of each element is picked and stored as the current envelope value according to Eq. 7 and Eq. 8 above.

At the end of each pulse-receive cycle, or acquisition period, the EEnv(i) for each of the elements are analyzed by the energy distribution and fault analyzer 1021 to see if the lowest EE(i) of any element constitutes a sudden drop compared to neighboring elements that could be indicative of a faulty element. If any sudden drop in EE(i) fits the predetermined criterion as described above in relation to functional block 1021 of FIG. 10, an alarm is sent by the faulty element alarm module 1020 indicating the faulty element.

The advantage of the above described alternative embodiment using envelope values is that the demand in computation is substantially decreased, because the routine shown in FIG. 10 for energy distribution and fault analyzer 1021 only needs to be run after each pulse-receive, or acquisition, cycle. It should also be noted that energy envelope embodiment may also be applied to phase compensated signals provided by step 1006 by means of phase adjusters 704 described above.

For design and operational efficiency, in this alternative embodiment of the present disclosure, data acquisition module 1202, energy level calculator 706 can reside within the same FPGA, which is preferably to be the existing FPGA that is used in a typical phased array system. The computation frequencies of both data acquisition module 1202 and energy level calculator 706 are higher than that of energy distribution and fault analyzer 1021, which runs at the end of each pulse-receive cycle, or acquisition period. Energy distribution and fault analyzer 1021, user interface module 114, and faulty element alarm module 1020 can be added to the micro processor that typically handles display or I/O control functions of conventional phased array instruments.

It can be appreciated by those skilled in the art that functional modules in FIGS. 1, 10 and 12 can be implemented by other types of hardware or software arranged in other fashions as it is deemed fit for design and operation of phased array instruments.

'Expected Energy Value' Alternate Embodiment

The 'expected energy value' (EEV) alternate embodiment uses a method that does not require the calculation and analysis of first or second order derivatives, as is required for three other embodiments previously mentioned in the present disclosure. Instead, the EEV embodiment depicted in FIGS. 11A and 11B uses a method that calculates the expected value, $E_e(i)$, by determining the magnitude of the midpoint between the E(i)'s adjacent to a particular E(i), and subsequently comparing $E_e(i)$ to E(i) to determine the presence of a substantial discontinuity.

$E_e(i)$ is calculated as follows by Eq. 5:

$$E_e(i) = E(i+1) + \{[E(i-1) - E(i+1)]/2\} \quad \text{Eq. 5}$$

To determine whether the deviation of E(i) with respect to $E_e(i)$ is substantial enough to be considered a faulty element, the percentage of variation of between them is weighted by the percentage of variation between its two neighbors. The latter percentage variation is a measure of the confidence level for the value of $E_e(i)$. The probability of E(i) being faulty is expressed by eq. 6 below.

$$P(E_i) = \frac{y1}{E_e(i)} * \left(1 - \frac{y2}{\max(E(i+1), E(i-1))}\right) \quad \text{Eq. 6}$$

Figure 11B:
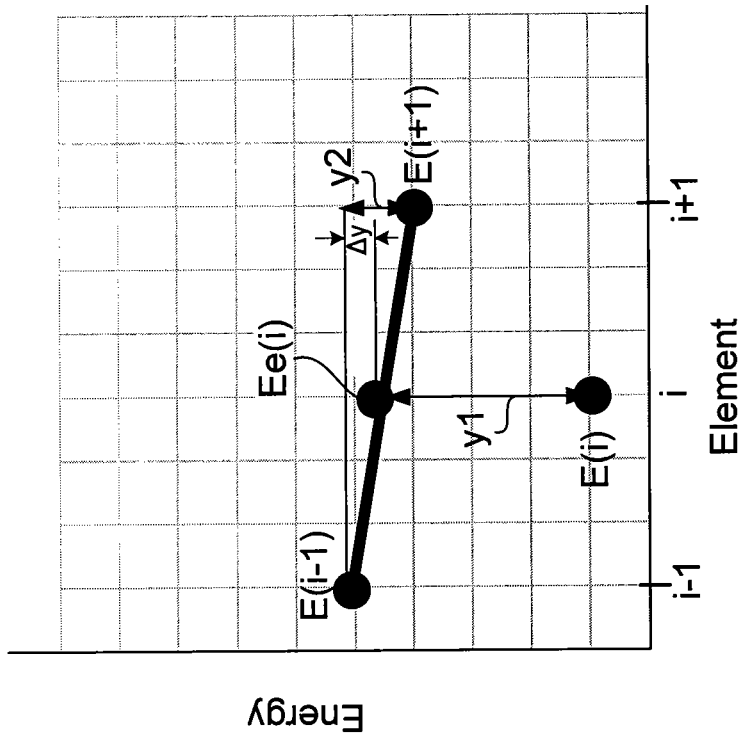
FIGS. 11A and 11B are diagrams showing an alternate embodiment of the phased array element fault providing an alternate method for identifying the sudden drop in the energy level among all elements by comparison to an expected energy value.

Referring again to FIGS. 11A and 11B, the deviation of E(i) with respect to $E_e(i)$ for both figures is the same; therefore, the first term of eq. 6 will be equal for both figures. In FIG. 11B, the second term of eq. 6 will be close to the value of one as y2 approaches zero. In this case, the confidence level on $E_e(i)$ is high because the two neighbors have close to the same amplitude. For FIG. 11A, the probability of detecting a faulty element is lower because the confidence of the expected value is lower due to y2 being much larger than the y2 of FIG. 11B. This causes the second term of eq. 6 to be much closer to zero.

To determine whether $P(E_i)$ is indicative of a faulty element, its value is compared to a predetermined threshold value, $T_{PEe}$, that once met causes the system to identify element i as a faulty element.

Figure 11A:
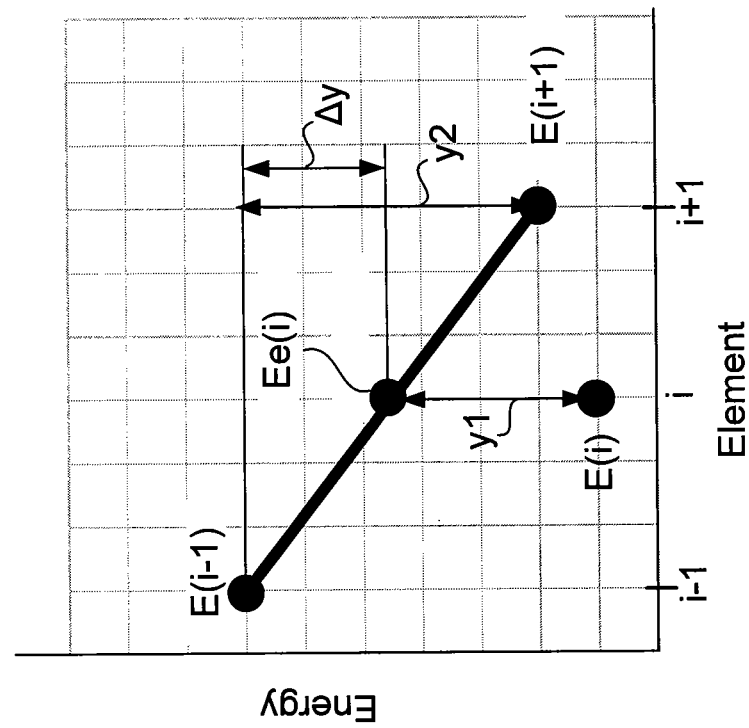

The next group of elements in FIGS. 11A and 11B consist of i, i+1, and i+2 (not shown). Accordingly, each successive group of three neighboring elements can be shifted by one, or more, elements until all elements to be evaluated are covered.

It can be appreciated by those skilled in the art that the expected energy level, $E_e(i)$, as disclosed in this alternate embodiment can be computed by many ways, including using the calculated energy level, E(i), of more than two neighboring elements and applying a curve fitting method.

The last, and simplest, alternate embodiment replaces steps 1015 through 1019 of FIG. 10 inclusively with a step (not shown) that evaluates each E(i), or EEnv(i), to determine whether it meets a predetermined magnitude threshold for a non-faulty element. If the threshold is not met, the process proceeds to create an alarm event by means of faulty element alarm 1020. because the element is considered to have a dropped energy level indicative of a faulty element. If the threshold is met, the process returns to step 1012.

It should be noted that for the purpose of establishing a higher confidence level for faulty element alarms, a predetermined number of alarms occurring at step 1020 may be required before the alarm event is reported to display and output 1011. The need for enabling and setting the parameters for this feature would typically be determined by the amount of signal noise in the reception signal.

Although the present invention has been described in relation to particular embodiments thereof, many other variations and modifications and other uses will become apparent to those skilled in the art. It is preferred, therefore, that the present invention not be limited by the specific disclosure herein.

What is claimed is:

1. A method of detecting faults in at least one transducer element of a phased array probe of an ultrasonic phased array instrument, the probe having a plurality of transducer elements, the method comprising:

applying ultrasonic pulses to and obtaining respective response signals from the transducer elements of the phased array probe as part of a normal operation of the phased array instruments;

calculating an average energy level E(i) at an element i for all the transducer elements individually according to an accumulated response signal reading obtained from the transducer elements individually during a predetermined time period;

noting a dropped energy level in one or more transducer elements owing to an element fault by identifying a large difference between the energy E(i) and an expected energy $E_e$ at the element i, wherein a line drawn between the energy of immediate neighboring elements, E(i−1) and E(i+1), and the expected energy $E_e$ is provided by the value when line E(i−1) and E(i+1) intersects with element i; and identifying any of the elements as a faulty element based on the energy level thereof.

2. The method of claim 1, including identifying the faulty element by comparing the energy level thereof to the energy levels sensed by other transducer elements.

3. The method of claim 1, further comprising identifying the dropped energy level by obtaining first order derivatives of the energy levels and obtaining a valley in the slope of the energy levels.

4. The method of claim 1, further comprising identifying the dropped energy level by obtaining second order derivatives of the energy levels and evaluating if any of the second order derivatives meets or exceeds a predetermined threshold value.

5. The method of claim 1, further comprising identifying an element fault by obtaining first order derivatives of the energy levels, further obtaining valleys in the slope of the energy levels with respect to elements and further determining a first element index number associated with a given valley;

obtaining second order derivatives of the energy levels and evaluating if any of the second order derivatives meets or exceeds a predetermined threshold value and further determining a second element index number associated with the second order derivatives of the energy levels that meets or exceeds the predetermined threshold value; and, if the first element index number equals the second element index number minus numeral 1, further determining the element associated with the first element index number is faulty.

6. The method of claim 1, further comprising recognizing and selecting the time period during which the drop in the energy level appears.

7. The method of claim 1, further comprising repetitively sampling the energy levels to include the time periods during which the drop in the energy level occurs.

8. The method of claim 1, further comprising identifying the drop in energy level in a manner avoiding an element blind spot.

9. The method of claim 1, wherein applying ultrasonic pulses to the transducer elements is provided with a phase shift with respect to the elements;

wherein calculating the energy level for the transducer elements is performed with the phase shift removed with respect to the elements.

10. A method of detecting transducer element faults in ultrasonic phased array instruments having a plurality of transducer elements, comprising:

applying ultrasonic pulses to the transducer elements of the phased array system;

calculating an energy level for the transducer elements individually according to a response signal reading obtained from the transducer elements individually during a predetermined time period;

noting a dropped energy level in one or more transducer elements owing to an element fault; and identifying any of the elements as a faulty element based on the energy level thereof, further comprising identifying the drop in energy level by obtaining a maximum value of the energy in each transducer element during a plurality of the predetermined time periods of a complete course of an ultrasonic phased array operation; and further identifying a drop in the maximum value of the energy in at least one of the transducer elements in comparison with the maximum values of energy levels of other transducer elements.

11. A system for detecting transducer element faults for ultrasonic phased array instruments, comprising:

a phased array transducer having a plurality of transducer elements operable to be pulsed by ultrasonic signals and to receive response signals;

an energy calculator operable to calculate an energy level of the response signals received from the transducer elements individually during a predetermined time period; and a fault analyzer operable to identify a drop in the energy level received on the transducer elements to identify a faulty element, by identifying in a large difference between the energy E(i) and an expected energy $E_e$ at an element i, wherein a line drawn between the energy of immediate neighboring elements, E(i−1) and E(i+1), and the expected energy $E_e$ is provided by the value when line E(i−1) and E(i+1) intersects with element i.

12. The system of claim 11, wherein the fault analyzer is operable to compare the energy levels with the energy levels received on remaining transducer elements, relative to the faulty transducer element.

13. The system of claim 11, wherein the phased array transducer is configured to be pulsed by ultrasonic signals and to receive response signals, as part of a normal operation of the ultrasonic phased array instrument.

14. The system of claim 11, wherein the fault analyzer is configured to detect the drop in the energy by obtaining first order derivatives of the energy levels and identifying a valley in the slope of the energy levels in a given element.

15. The system of claim 11, wherein the fault analyzer is configured to detect the drop in the energy level by obtaining second order derivatives of the energy levels and evaluating if the absolute value of any of the second order derivatives exceeds a predetermined threshold value.

16. The system of claim 11, wherein the fault analyzer is configured to detect the drop in the energy level by obtaining first order derivatives of the energy levels, further obtaining valleys in the slope of the energy levels with respect to elements and further determining a first element index number associated with a given valley;

obtaining second order derivatives of the energy levels and evaluating if any of the second order derivatives meets or exceeds a predetermined threshold value and further determining a second element index number associated with the second order derivatives of the energy levels that meets or exceeds the predetermined threshold value; and, if the first element index number equals the second element index number minus numeral 1, further determining the element associated with the first element index number is faulty.

17. A system for detecting transducer element faults for ultrasonic phased array instruments, comprising:
- a phased array transducer having a plurality of transducer elements operable to be pulsed by ultrasonic signals and to receive response signals;
- an energy calculator operable to calculate an energy level of the response signals received from the transducer elements individually during a predetermined time period; and
- a fault analyzer operable to identify a drop in the energy level received on the transducer elements to identify a faulty element, by obtaining a maximum value of the energy level in each transducer element of a plurality of the predetermined time periods while performing normal ultrasonic phased array tests; and
- to further identify the drop in the maximum value of the energy levels in at least one transducer element in comparison with the maximum value of the energy levels of other transducer elements.

* * * * *